United States Patent [19]

Yanagawa et al.

[11] Patent Number: 5,041,511

[45] Date of Patent: Aug. 20, 1991

[54] OCULAR LENS MATERIAL

[75] Inventors: Hiroaki Yanagawa; Naotaka Kamiya, both of Nagoya, Japan

[73] Assignee: Menicon Co., Ltd., Nagoya, Japan

[21] Appl. No.: 462,547

[22] Filed: Jan. 9, 1990

[30] Foreign Application Priority Data

Jan. 26, 1989 [JP] Japan ................... 1-16620

[51] Int. Cl.$^5$ .............................. C08F 18/16
[52] U.S. Cl. .................. 526/326; 526/245; 526/279; 350/409
[58] Field of Search ............ 526/326, 245, 279

[56] References Cited

U.S. PATENT DOCUMENTS

| | | | |
|---|---|---|---|
| 3,882,084 | 5/1975 | Tato et al. | 526/326 |
| 3,924,044 | 12/1975 | Gobran et al. | 526/326 |
| 4,393,184 | 7/1983 | Tarumi et al. | 526/326 |
| 4,709,000 | 11/1987 | Wenzel et al. | 526/326 |
| 4,777,632 | 10/1988 | Wenzel et al. | 526/326 |

FOREIGN PATENT DOCUMENTS

| | | | |
|---|---|---|---|
| 59-122566 | 7/1984 | Japan | 526/326 |
| 62-10121 | 1/1987 | Japan | 526/326 |
| 536722 | 5/1941 | United Kingdom | 526/326 |
| 651355 | 3/1951 | United Kingdom | 526/326 |
| 850311 | 10/1960 | United Kingdom | 526/326 |
| 962109 | 6/1964 | United Kingdom | 526/326 |

*Primary Examiner*—Joseph L. Schofer
*Assistant Examiner*—N. Sarofim
*Attorney, Agent, or Firm*—Oblon, Spivak, McClelland, Maier & Neustadt

[57] ABSTRACT

An ocular lens material, wherein a cross linking agent of the formula:

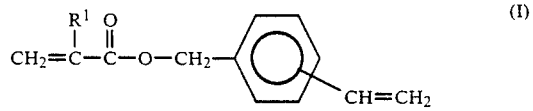

wherein $R^1$ is a hydrogen atom or a methyl group, is used.

5 Claims, No Drawings

OCULAR LENS MATERIAL

The present invention relates to a material for ocular lenses (such as contact lenses, intraocular lenses or artificial cornea) having excellent optical properties and high strength. Further, the present invention relates to an ocular lens material useful as a contact lens material which is excellent not only in the optical properties and strength but also in the oxygen permeability.

In the synthesis of a copolymer to be used as an ocular lens material, a cross linking agent has been used to let the copolymer have a cross linked network structure and to make it tough.

However, particularly in the synthesis of a copolymer comprising a styrene monomer, and an acrylic monomer and/or a methacrylic monomer (hereinafter referred to as a (meth)acrylic monomer), particularly a copolymer comprising them in a weight ratio within a range of from 10:90 to 70:30, if the copolymer is synthesized by means of a conventional cross linking agent such as ethylene glycol dimethacrylate, allyl methacrylate, trimethylolpropane trimethacrylate or divinyl benzene, the composition of the polymer tends to be non-uniform due to the difference in the polymerization rate or in the compatibility during the polymerization process. Consequently, the resulting material (copolymer) will be non-uniform, lack in optical transparency and have turbidity or optical distortion. For example, in a system wherein a styrene monomer and a (meth)acrylic monomer are copolymerized substantially stoichiometrically, turbidity will be distinctly formed if such a conventional cross linking agent is used.

Further, in the case of an ocular lens material having high oxygen permeability, which has attached an attension as a prospective material for an oxygen permeable hard contact lens, there is a difficulty such that when it is attempted to increase the oxygen permeability, the mechanical strength and the hardness tend to decrease even if a conventional cross linking agent is used in an optimum amount, and the material tends to be brittle if the cross linking agent is used excessively, whereby it tends to be weak against an impact or other stress.

The present invention has been made to solve the above problems, and the object of the present invention is to obtain an ocular lens material made of a copolymer having a cross linked network structure, which is tough and optically transparent without optical distortion, particularly an ocular lens material composed of a styrene monomer and a (meth)acrylic monomer, which is tough and has excellent mechanical strength and hardness and which is transparent and excellent in the optical properties without optical distortion.

A further object of the present invention is to provide an ocular lens material useful as a contact lens material which is optically transparent without distortion and has a high refractive index and excellent mechanical strength and hardness and superior durability against an impact and which has an excellent oxygen permeability.

The present invention provides an ocular lens material, wherein a cross linking agent of the formula:

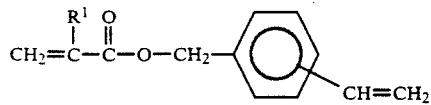

(I)

wherein $R^1$ is a hydrogen atom or a methyl group, is used.

Now, the present invention will be described in detail with reference to the preferred embodiments.

The ocular lens material of the present invention is a copolymer wherein a vinylbenzyl acrylate and/or a vinylbenzyl methacrylate (hereinafter referred to as a vinylbenzyl (meth)acrylate) of the above formula I is used as the cross linking agent.

The above-mentioned vinylbenzyl (meth)acrylate is a cross linkable monomer having an acryloyl group or a methacryloyl group (hereinafter referred to as a (meth)acryloyl group) and a vinyl group bonded to a benzene ring, as functional groups. Specific examples thereof include, for example, 4-vinylbenzyl (meth)acrylate and 3-vinylbenzyl (meth)acrylate. These vinylbenzyl (meth)acrylates may be used alone or in combination as a mixture of two or more different types.

Such a vinylbenzyl (meth)acrylate serves to let the copolymer have a cross linked structure so that it will be tough and will have improved mechanical strength and hardness and make an ocular lens material which is uniform and transparent without turbidity and which has excellent optical properties without optical distortion. Further, it provides other cross linking effects such as effects to improve durability such as chemical resistance, heat resistance, solvent resistance or dimension stability and to reduce eluting substances.

Such a vinylbenzyl (meth)acrylate can be prepared, for example, by reacting acrylic acid or methacrylic acid (hereinafter referred to as (meth)acrylic acid) and chloromethylstyrene in the presence of 1,8-diazabicyclo[5.4.0]-7-undecene.

The obtained vinylbenzyl methacrylate is a colorless transparent liquid having an aroma and a boiling point of from 90 to 105° C. (under 0.12 mmHg), and the vinylbenzyl acrylate is a colorless transparent liquid having an aroma and a boiling point of from 80 to 90° C. (under 0.10 mmHg). Their structures can be confirmed by a $^1$H-NMR spectrum method, an infrared absorption spectrum method, etc.

The monomers to be used together with the cross linking agent of the formula I as components of the ocular lens material of the present invention, include a (meth)acrylic monomer, a styrene monomer and other monomers.

Particularly when a copolymer is synthesized by using a (meth)acrylic monomer and a styrene monomer together with the cross linking agent of the formula I, the cross linking agent will be uniformly mixed and polymerized with these monomers, since the (meth)acryloyl group portion of the cross linking agent has good compatibility with the (meth)acrylic monomer, and the vinyl group bonded to the benzene ring i.e. the so-called styrene backbone portion has good compatibility with the styrene monomer. Although there is a difference in the polymerization rate between the (meth)acryloyl group of the (meth)acrylic monomer and the vinyl group of the styrene monomer, the cross linking agent of the formula I polymerizes excellently with the copolymer components (i.e. the (meth)acrylic monomer and the styrene monomer) having functional groups (i.e. the (meth)acryloyl group and the vinyl group) having substantially the same polymerization rates as the two functional groups of the cross linking agent i.e. the (meth)acryloyl group and the vinyl group bonded to the benzene ring, respectively.

Accordingly, if the cross linking agent of the formula I is used for the preparation of a copolymer of the (meth)acrylic monomer and the styrene monomer, the copolymerization proceeds smoothly to form a cross linked structure, whereby the resulting copolymer will be tough and will have improved mechanical strength and hardness, and it will be a material which is uniform and transparent without turbidity and which has excellent optical properties without optical distortion.

Specific examples of the (meth)acrylic monomer include linear, branched and cyclic alkyl (meth)acrylates such as methyl (meth)acrylate, ethyl (meth)acrylate, n-propyl (meth)acrylate, isopropyl (meth)acrylate, n-butyl (meth)acrylate, tert-butyl (meth)acrylate, isobutyl (meth)acrylate, pentyl (meth)acrylate, tert-pentyl (meth)acrylate, hexyl (meth)acrylate, 2-methylbutyl (meth)acryalte, heptyl (meth)acrylate, octyl (meth)acrylate, 2-ethylhexyl (meth)acrylate, nonyl (meth)acrylate, decyl (meth)acrylate, dodecyl (meth)acrylate, stearyl (meth)acrylate, cyclopentyl (meth)acrylate and cyclohexyl (meth)acrylate; silicon-containing (methy)acrylates such as pentamethyldisiloxanylmethyl (meth)acrylate, pentamethyldisiloxanylpropyl (meth)acrylate, methylbis(trimethylsiloxy)silylpropyl (meth)acrylate, tris(trimethylsiloxy)silylpropyl (meth)acrylate, mono[methylbis(trimethylsiloxy)siloxy]bis(trimethylsiloxy)silylpropyl (meth)acrylate, tris[methylbis(trimethylsiloxy)siloxy]silylpropyl (meth)acrylate, methylbis(trimethylsiloxy)silylpropyl glyceryl (meth)acrylate, tris(trimethylsiloxy)silylpropylglyceryl (meth)acrylate, mono[methylbis(trimethylsiloxy)siloxy]bis(trimethylsiloxy)silylpropylglyceryl (meth)acrylate, trimethylsilylethyltetramethyldisiloxanylpropylglyceryl (meth)acrylate, trimethylsilylmethyl (meth)acrylate, trimethylsilylpropyl (meth)acrylate, trimethylsilylpropylglyceryl (meth)acrylate, pentamethyldisiloxanylpropylglyceryl (meth)acrylate, methylbis(trimethylsiloxy)silylethyltetramethyl disiloxanylmethyl (meth)acrylate, tetramethyltriisopropylcyclotetrasiloxanylpropyl (meth)acrylate and tetramethyltriisopropylcyclotetrasiloxybis(trimethylsiloxy)silylpropyl (meth)acrylate; fluorine-containing (meth)acrylates of the formula II:

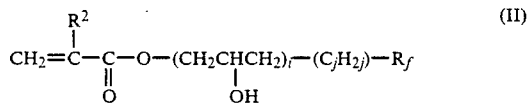

wherein $R^2$ is a hydrogen atom or a methyl group, $R_f$ is a linear or branched fluoroalkyl group having from 2 to 21 fluorine atoms, i is 0 or 1, and j is an integer of from 0 to 3, such as 2,2,2-trifluoroethyl (meth)acrylate, 2,2,3,3-tetrafluoropropyl (meth)acrylate, 2,2,3,3,3-pentafluoropropyl (meth)acrylate, 2,2,2-trifluoro-1-trifluoromethylethyl (meth)acrylate, 2,2,3,3-tetrafluoro-tert-pentyl (meth)acrylate, 2,2,3,4,4,4-hexafluorobutyl (meth)acrylate, 2,2,3,3,4,4-hexafluorobutyl (meth)acrylate, 2,2,3,4,4,4-hexafluoro-tert-hexyl (meth)acrylate, 2,2,3,3,4,4,4-heptafluorobutyl (meth)acrylate, 2,2,3,3,4,4,5,5-octafluoropentyl (meth)acrylate, 2,3,4,5,5,5-hexafluoro-2,4-bis(trifluoromethyl)pentyl (meth)acrylate, 2,2,3,3,4,4,5,5,5-nonafluoropentyl (meth)acrylate, 2,2,3,3,4,4,5,5,6,6,7,7-dodecafluoroheptyl (meth)acrylate, 3,3,4,4,5,5,6,6,7,7,8,8-dodecafluorooctyl (meth)acrylate, 3,3,4,4,5,5,6,6,7,7,8,8,8-tridecafluorooctyl (meth)acrylate, 2,2,3,3,4,4,5,5,6,6,7,7,7-tridecafluoroheptyl (meth)acrylate, 3,3,4,4,5,5,6,6,7,7,8,8,9,9,10,10-hexadecafluorodecyl (meth)acrylate, 3,3,4,4,5,5,6,6,7,7,8,8,9,9,10,10,10-heptadecafluorodecyl (meth)acrylate, 3,3,4,4,5,5,6,6,7,7,8,8,9,9,10,10,11,11-octadecafluoroundecyl (meth)acrylate, 3,3,4,4,5,5,6,6,7,7,8,8,9,9,10,10,11,11,11-nonadecafluoroundecyl (meth)acrylate, 3,3,4,4,5,5,6,6,7,7,8,8,9,9,10,10,11,11,12,12-eicosafluorodecyl 4,4,5,5,6,7,7,7-octafluoro-6-trifluoromethylheptyl (meth)acrylate, 2-hydroxy-4,4,5,5,6,6,7,7,8,9,9,9-dodecafluoro-8-trifluoroethylnonyl (meth)acrylate and 2-hydroxy-4,4,5,5,6,6,7,7,8,8,9,9,10,11,11,11-hexadecafluoro-1-trifluoromethylundecyl (meth)acrylate; hydroxyl group-containing (meth)acrylates such as hydroxyethyl (meth)acrylate, hydroxypropyl (meth)acrylate, hydroxybutyl (meth)acrylate, dihydroxypropyl (meth)acrylate, dihydroxybutyl (meth)acrylate, diethyleneglycol mono(meth)acrylate, triethyleneglycol mono(meth)acrylate and dipropylene glycol mono(meth)acrylate; (meth)acrylic acid; N-(meth)acryloylpyrrolidone; (meth)acrylamides such as (meth)acrylamide, N-methyl (meth)acrylamide, N-ethyl (meth)acrylamide, N-hydroxyethyl (meth)acrylamide, N,N-dimethyl (meth)acrylamide, N,N-diethyl (meth)acrylamide and N-ethylaminoethyl (meth)acrylamide; aminoalkyl (meth)acrylates such as aminoethyl (meth)acrylate, N-methylaminoethyl (meth)acrylate and N,N-dimethylaminoethyl (meth)acrylate; alkoxy group-containing (meth)acrylates such as methoxyethyl (meth)acrylate, ethoxyethyl (meth)acrylate and methoxydiethyleneglycol (meth)acrylate; aromatic group-containing (meth)acrylates such as benzyl (meth)acrylate; glycidyl (meth)acrylate; tetrahydrofurfuryl (meth)acrylate; N-(meth)acryloylpiperidine; N-(meth)acryloylmorpholine; 2-cyanoethyl (meth)acrylate; benzophenone polymerizable ultraviolet absorbers such as 2-hydroxy-4-(meth)acryloyloxybenzophenone, 2-hydroxy-4-(meth)acryloyloxy-5-tert-butylbenzophenone, 2-hydroxy-4-(meth)acryloyloxy-2',4'-dichlorobenzophenone and 2-hydroxy-4-(2'-hydroxy-3'-(meth)acryloyloxypropoxy)-benzophenone; benzotriazole type polymerizable ultraviolet absorbers such as 2-(2'-hydroxy-5'-(meth)acryloyloxyethylphenyl)-2H-benzotriazole, 2-(2'-hydroxy-5'(meth)acryloyloxyethylphenyl)-5-chloro-2H-benzotriazole, 2-(2'-hydroxy-5'-(meth)acryloyloxypropylphenyl)-2H-benzotriazole and 2-(2'-hydroxy-5'-(meth)acryloyloxypropyl-3'-tert-butylphenyl)-5-chloro-2H-benzotriazole; salicylic acid derivative type polymerizable ultraviolet absorbers such as phenyl 2-hydroxy-4-(meth)acryloyloxymethylbenzoate; polymerizable ultraviolet absorbers such as 2-cyano-3-phenyl-3-(3'-(meth)acryloyloxyphenyl)propenoic acid methyl ester; azo type polymerizable dyes such as 1-phenylazo-4-(meth)acryloyloxynaphthalene, 1-phenylazo-2-hydroxy-3-(meth)acryloyloxynaphthalene, 1-naphthylazo-2-hydroxy-3-(meth)acryloyloxynaphthalene, 1-(α-anthrylazo)-2-hydroxy-3-(meth)acryloloxynaphthalene, 1-((4'-(phenylazo)phenyl)azo)-2-hydroxy-3-(meth)acryloyloxynaphthalene, 1-(2',4'-xylylazo)-2(meth)acryloyloxynaphthalene, 1-(o-tolylazo)-2-(meth)acryloyloxynaphthalene, 2-(m-(meth)acryloylamideanilino)-4,6-bis(1'-(o-tolylazo)-2'-naphthylamino)-1,3,5 triazine, 3-(meth)acryloylamide-4-phenylazophenol, 3-(meth)acryloylamide-4-(8'-hydroxy-3',6'-disulfo-1'-naphthylazo)phenol, 3-(meth)acryloylamide-4-(1'-phenylazo-2'-naphthylazo)phenol, 3-(meth)acryloylamide-4-(p-tolylazo)phenol and 4- phenylazo-7-(meth)acryloylamide-1-naphthol; anthraquinone type polymerizable dyes such as 1,5-bis((meth)acryloylamino)-9,10 anthraquinone, 1-amino-4-(3'-(meth)acryloylaminophenylamino)-9,10-anthraquinone-2-sulfonic acid, 1-amino-4-(3'-(meth)acryloylaminobenzylamino)-9,10-anthraquinone-2-sulfonic acid, 2-(3'-(meth)acryloylamide-anilino-4 (3'(3''-sulfo-4''-aminoanthraquinone-1''-yl)-amino-anilino)-6-chloro-1,3,5-triazine and 2-(3'-(meth)acryloylamide-anilino)-4-(3'-(3''-sulfo-4''-aminoanthraquinone-1''-yl)-amino-anilino)-6-hydradino-1,3,5-triazine; nitro-type polymerizable dyes such as o-nitroanilinomethyl (meth)acrylate; phthalocyanine type polymerizable dyes such as (meth)acryloyl-modified tetraamino copper phthalocyanine and (meth)acryloyl-modified (dodecanoyl-modified tetraamino copper phthalocyanine); and polymerizable ultraviolet absorptive dyes such as
2,4-dihydroxy-3-(p-(meth)acryloyloxymethyl-phenylazo)benzophenone,
2,4-dihydroxy-5-(p-(meth)acryloyloxymethyl-phenylazo)benzophenone,
2,4-dihydroxy-5-(p-(meth)acryloyloxyethylphenylazo)-benzophenone,
2,4-dihydroxy-5-(p-(meth)acryloyloxyethylphenylazo)-benzophenone,
2,4-dihydroxy-3-(p-(meth)acryloyloxypropyl-phenylazo)benzophenone,
2,4-dihydroxy-5-(p-(meth)acryloyloxypropyl-phenylazo)benzophenone,
2,4-dihydroxy-3-(o-(meth)acryloyloxymethyl-phenylazo)benzophenone,
2,4-dihydroxy-5-(o-(meth)acryloyloxymethyl-phenylazo)benzophenone,
2,4-dihydroxy-3-(o-(meth)acryloyloxyethylphenylazo)-benzophenone,
2,4-dihydroxy-5-(o-(meth)acryloyloxyethylphenylazo)-benzophenone,
2,4-dihydroxy-3-(o-(meth)acryloyloxypropyl-phenylazo)benzophenone,
2,4-dihydroxy-5-(o-(meth)acryloyloxypropyl-phenylazo)benzophenone,
2,4-dihydroxy-3-(p-(N,N-di(meth)acryloyloxyethylamino)phenylazo)benzophenone,
2,4-dihydoxy-5-(p-(N,N-di(meth)acryloyloxyethylamino)phenylazo)benzophenone,
2,4-dihydroxy-3-(o-(N,N-di(meth)acryloyloxyethylamino)phenylazo)benzophenone,
2,4-dihydroxy-5-(o-(N,N-di(meth)acryloyloxyethylamino)phenylazo)benzophenone,
2,4-dihydroxy-3-(p-(N-ethyl-N-(meth)acryloyloxyethylamino)phenylazo)benzophenone,
2,4-dihydroxy-5-(p-(N-ethyl-N-(meth)acryloyloxyethylamino)phenylazo)benzophenone,
2,4-dihydroxy-3-(o-(N-ethyl-N-(meth)acryloyloxyethylamino)phenylazo)benzophenone,
2,4-dihydroxy-5-(o-(N-ethyl-N-(meth)acryloyloxyethylamino)phenylazo)benzophenone,
2,4-dihydroxy-3-(p-(N-ethyl-N-(meth)acryloylamino)-phenylazo)benzophenone,
2,4-dihydroxy-5-(p-(N-ethyl-N-(meth)acryloylamino)-phenylazo)benzophenone,
2,4-dihydroxy-3-(o-(N-ethyl-N-(meth)acryloylamino)-phenylazo)benzophenone, and
2,4-dihydroxy-5-(o-(N-ethyl-N-(meth)acryloylamino)-phenylazo)benzophenone.

These (meth)acrylic monomers may be used alone or in combination as a mixture of two or more different kinds.

In the above specific examples, a (meth)acrylate means an acrylate and/or a methacrylate. The same applies to other (meth)acrylic derivatives.

Specific examples of the styrene monomer include, for example, silicon-containing styrene derivatives of the formula III:

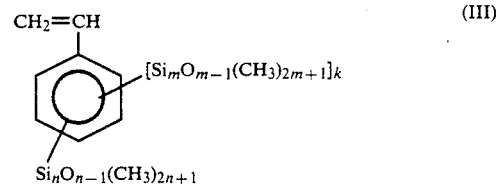

wherein k is 0 or 1, m is an integer of from 1 to 15 and n is an integer of from 1 to 15, such as
tris(trimethylsiloxy)silylstyrene,
bis(trimethylsiloxy)methylsilylstyrene,
(trimethylsiloxy)dimethylsilylstyrene,
trimethylsilylstyrene,
tris(trimethylsiloxy)siloxanyldimethylsilylstyrene,
[bis(trimethylsiloxy)methylsiloxanyl]dimethylsilylstyrene,
pentamethyldisiloxanylstyrene,
heptamethyltrisiloxanylstyrene,
nonamethyltetrasiloxanylstyrene,
pentadecamethylheptasiloxanylstyrene,
heneicosamethyldecasiloxanylstyrene,
heptacosamethyltridecasiloxanylstyrene,
hentriacontamethylpentadecasiloxanylstyrene,
trimethylsiloxy pentamethyldisiloxy.methylsilylstyrene,
tris(pentamethyldisiloxy)silylstyrene,
(tris.trimethylsiloxy)siloxanyl.bis(trimethylsiloxy)silylstyrene,
bis(heptamethyltrisiloxy)methylsilylstyrene,
tris(methylbis.trimethylsiloxy.siloxy)silylstyrene,
trimethylsiloxy.bis(tris.trimethylsiloxy.siloxy)silystyrene,
heptakis(trimethylsiloxy)trisiloxanylstyrene,
nonamethyltetrasiloxy undecylmethylpentasiloxy methylsilylstyrene,
tris(tris.trimethylsiloxy.siloxy)silylstyrene,
(tristrimethylsiloxy.hexamethyl)tetrasiloxy.(tris.trimethylsiloxy)siloxy.trimethylsiloxysilylstyrene,
nonakis(trimethylsiloxy)tetrasiloxanylstyrene,
bis(tridecamethylhexasiloxy)methylsilylstyrene,
heptamethylcyclotetrasiloxanylstyrene,
heptamethylcyclotetrasiloxy.bis(trimethylsiloxy)silylstyrene and
tripropyltetramethylcyclotetrasiloxanylstyrene;
fluorine-containing styrene derivatives such as o-fluorostyrene, m-fluorostyrene, p-fluorostyrene, trifluorostyrene, perfluorostyrene, p-trifluoromethylstyrene, o-trifluoromethylstyrene and m-trifluoromethylstyrene; and styrene derivatives such as o-methylstyrene, m-methylstyrene, p-methylstyrene, p-ethylstyrene, o-hydroxystyrene, m-hydroxystyrene, p-hydroxystyrene, trimethylstyrene, tert-butylstyrene, perbromostyrene, dimethylaminostyrene and α-methylstyrene. These styrene monomers may be used alone or in combination as a mixture of two or more different types.

Further, vinyl monomers containing a vinyl group other than the above-mentioned styrene monomers, may be used as equivalent to the styrene monomers. Specific examples of such vinyl monomers include, for example, vinyllactams, such as N-vinylpyrrolidone, α-methylene-N-methylpyrrolidone and N-vinylcaprolactam; 4-vinylpyridine; hetero ring type N-vinyl monomers such as N-vinylimidazole, N-vinylpiperidone, N-vinylpiperidine and N-vinylsuccinimide; azo type polymerizable dyes such as 2-(m-vinylanilino)-4-((p-nitrophenylazo)-anilino)-6-chloro-1,3,5-triazine, 2-(1'-(o-tolylazo)-2-(1'-(o-tolylazo)-2'-naphthyloxy)-4-(m-vinylanilino)-6-chloro-1,3,5-triazine, 2-(p-vinylanilino)-4-(1'-(o-tolylazo)-2'-naphthylamino)-6-chloro-1,3,5-triazine, N-(1'-(o-tolylazo)-2'-naphthyl)3-vinylphthalic acid monoamide, N-(1'-(o-tolylazo)-2'-naphthyl)-6-vinylphthalic acid monoamide, 3-vinylphthalic acid-(4'-(p-sulfophenylazo)-1'-naphthyl)monoester, 6-vinylphthalic acid-(4'-(p-sulfophenylazo)-1'-naphthyl)monoester, 2-amino-4-(m-(2'-hydroxy-1'-naphthylazo)anilino)-6-isopropenyl-1,3,5-triazine, 2-amino-4-(N-methyl-p-(2'-hydroxy-1'-naphthylazo)anilino)-6-isopropenyl-1,3,5-triazine, 2-amino-4-(N-methyl-p-(2'-hydroxy-1'-naphthylazo)anilino)-6-isopropenyl-1,3,5-triazine, 2-amino-4-(m-(4'-hydroxy-1'-phenylazo)anilino)-6-isopropenyl-1,3,5-triazine, 2-amino-4-(N-methyl-p-(4'-hydroxyphenylazo)anilino)-6-isopropenyl-1,3,5-triazine, 2-amino-4-(m-(3'-methyl-1'-phenyl-5'-hydroxy-4'-pyrazolylazo)anilino)-6-isopropenyl1,3,5-triazine, 2-amino-4-(N-methyl-p-(3'-methyl-1'-phenyl-5'hydroxy-4'-pyrazolylazo)anilino)-6-isopropenyl1,3,5-triazine and 2-amino-4-(p-phenylazoanilino)-6-isopropenyl-1,3,5-triazine; anthraquinone type polymerizable dyes such as 1-(4'-vinylbenzoylamide)-9,10-anthraquinone, 4-amino-1-(4'-vinylbenzoylamide)-9,10-anthraquinone, 5-amino-1-(4'-vinylbenzoylamide)-9,10-anthraquinone, 8-amino-1-(4'-vinylbenzoylamide)-9,10-anthraquinone, 4-nitro-1-(4'-vinylbenzoylamide)-9,10-anthraquinone, 4-hydroxy-1-(4'-vinylbenzoylamide)-9,10-anthraquinone, 1-(2'-vinylbenzoylamide)-9,10-anthraquinone, 1-(4'-isopropenylbenzoylamide)-9,10-anthraquinone, 1-(3'-isopropenylbenzoylamide)-9,10-anthraquinone, 1-(2'-isopropenylbenzoylamide)-9,10-anthraquinone, 1,4-bis-(4'-vinylbenzoylamide)-9,10-anthraquinone, 1,4-bis-(4'-isopropenylbenzoylamide)-9,10-anthraquinone, 1,5-bis-(4'-vinylbenzoylamide)-9,10-anthraquinone, 1,5-bis-(4'-isopropenylbenzoylamide)-9,10-anthraquinone, 1-methylamino-4-(3'-vinylbenzoylamide)-9,10-anthraquinone, 1-methylamino-4-(4'-vinylbenzoyloxyethylamino)-9,10-anthraquinone, 1-amino-4(3'-vinylphenylamino)-9,10-anthraquinone-2-sulfonic acid, 1-amino-4-(4'-vinylphenylamino)-9,10-anthraquinone-2sulfonic acid, 1-amino-4-(2'-vinylbenzylamino)-9,10-anthraquinone-2-sulfonic acid, 1-(β-ethoxycarbonylallylamino-9,10-anthraquinone, 1-(β-carboxyallylamino)-9,10-anthraquinone, 1,5-di-(β-carboxyallylamino)-9,10-anthraquinone, 1-(β-isopropoxycarbonylallylamino)-5-benzoylamide-9,10-anthraquinone, 2,4-bis-((4''-methoxyanthraquinone-1''-yl)-amino)-6-(3'-vinylanilino)-1,3,5-triazine and 2-(2'-vinylphenoxy-(4-(4'-(3''-sulfo-4''-aminoanthraquinone- '1'''-yl-amino)-anilino)-6-chloro-1,3,5-triazine; and polymerizable ultraviolet absorptive dyes such as 2,4-dihydroxy-3-(p-styrenoazo)benzophenone, 2,4-dihydroxy-5-(p-styrenoazo)benzophenone and phenyl 2-hydroxy-4-(pstyrenoazo)benzoate. These vinyl monomers may be used alone or in combination as a mixture of two or more different types.

A conventional cross linking agent may also be used as an assistant for the ocular lens material of the present invention, taking into accounts the types and amounts of the copolymer components or the nature of the desired copolymer. Specific examples of such a conventional cross linking agent include, for example, ethylene glycol di(meth)acrylate, diethylene glycol di(meth)acrylate, triethylene glycol di(meth)acrylate, propylene glycol di(meth)acrylate, dipropylene glycol di(meth)acrylate, allyl (meth)acrylate, vinyl (meth)acrylate, trimethylolpropane tri(meth)acrylate, methacryloyloxyethyl acrylate, divinylbenzene, diallyl phthalate, diallyl azipate, triallyl isocyanurate, α-methylene-N-vinylpyrrolidone, 2,2-bis(p-(meth)acryloyloxyphenyl)hexafluoropropane, 2,2-bis(m-(meth)acryloyloxyphenyl)hexafluoropropane, 2,2-bis(o-(meth)acryloyloxyphenyl)hexafluoropropane, 2,2-bis(m-(meth)acryloyloxyphenyl)propane, 2,2-bis(o-(meth)acryloyloxyphenyl)propane, 1,4-bis(2-(meth)acryloyloxyhexafluoroisopropyl)benzene, 1,3-bis(2-(meth)acryloyloxyhexafluoroisopropyl)benzene, 1,2-bis(2-(meth)acryloyloxyhexafluoroisopropyl)benzene, 1,4-bis(2-(meth)acryloyloxyisopropyl)benzene, 1,3-bis(2-(meth)acryloyloxyisopropyl)benzene and 1,2-bis(2-(meth)acryloyloxyisopropyl)benzene. These conventional cross linking agents may be used alone or in combination as a mixture of two or more different types.

The proportion of the cross linking agent of the formula I in the ocular lens material of the present invention is preferably within a range of from about 0.5 to 15 parts by weight, more preferably from 2 to 10 parts by weight, in 100 parts by weight of the total amount of the copolymer components used. If the cross linking agent exceeds 15 parts by weight, the physical properties attributable to other monomer components for polymerization, such as the oxygen permeability, tend to be low, and the material thereby obtained tends to be brittle and weak against a stress such as an impact. On the other hand, if the amount is less than 0.5 part by weight, a distortion is likely to result and a turbidity is likely to form in the resulting material, and the ocular lens material tends to be non-uniform and lack in optical transparency, and thus the effects of using the cross linking agent tend to be low.

The types, the number and the amounts of monomers as components of the ocular lens material of the present invention other than the cross linking agent of the formula I, may optionally be selected depending upon the physical properties or the nature of the desired ocular lens material.

For example, to obtain a contact lens material having good oxygen permeability, a silicon-containing monomer or a fluorine-containing monomer, preferably a silicon-containing (meth)acrylate, a silicon-containing styrene derivative, a fluorine-containing (meth)acrylate or a fluorine-containing styrene derivative, may be selected.

To improve the strength of a lens and to obtain an ocular lens material having high strength, an alkyl (meth)acrylate, styrene, a styrene derivative or (meth)acrylic acid may preferably be selected.

To impart hydrophilicity to a lens or to obtain a water absorptive soft ocular lens material, a monomer having a hydrophilic group, preferably a hydroxyl group-containing (meth)acrylate, (meth)acrylamide, aminoalkyl (meth)acrylate, (meth)acrylic acid or N-vinyllactam, may be selected.

To obtain an ocular lens material scarcely stained with lipids, a fluorine-containing monomer, preferably a fluorine-containing (meth)acrylate or a fluorine-containing styrene derivative, may be selected.

To obtain an ocular lens material having a high refractive index, a monomer containing an aromatic ring, preferably a styrene monomer, may be selected.

To impart an ultraviolet absorptivity to the material or to color the material, a monomer may be suitably selected from polymerizable ultraviolet absorbers, polymerizable dyes and polymerizable ultraviolet absorptive dyes.

Among them, an ocular lens material comprising a silicon-containing styrene derivative, a fluorine-containing (meth)acrylate and the cross linking agent of the formula I as essential components, is particularly preferably used as a contact lens material, since it is optically transparent without optical distortion and has a high refractive index and excellent mechanical strength and hardness and thus is excellent in the durability against an impact, and yet it is a material having excellent oxygen permeability. The proportion of such a silicon-containing styrene derivative and a fluorine-containing (meth)acrylate in the ocular lens material is preferably within a range of from 40 to 99.5 parts by weight, more preferably within a range of from 50 to 98 parts by weight, in 100 parts by weight of the total amount of the copolymer components, with a view to obtaining a contact lens material which is optically transparent without optical distortion and has a high refractive index and excellent mechanical strength and hardness and thus is excellent in the durability against an impact and which has excellent oxygen permeability. Further, when the total amount of the silicon-containing styrene derivative and the fluorine-containing (meth)acrylate is 100 parts by weight, the silicon-containing styrene derivative is preferably within a range of from 5 to 95 parts by weight, and the fluorine-containing (meth)acrylate is preferably within a range of from 5 to 95 parts by weight. Further, the silicon-containing styrene derivative is more preferably within a range of from 30 to 90 parts by weight, and the fluorine-containing (meth)acrylate is more preferably within a range of from 10 to 70 parts by weight. Particularly preferably, the silicon-containing styrene derivative is at least 30 parts by weight in 100 parts by weight of the styrene monomer as a copolymer component, and the fluorine-containing (meth)acrylate is at least 40 parts by weight in 100 parts by weight of the (meth)acrylate monomer as a copolymer component.

The ocular lens material of the present invention is prepared by a method which is commonly employed in this technical field by uniformly mixing the cross linking agent of the formula I with various monomer components (such as the (meth)acrylate monomer and the styrene monomer) and adding a polymerization initiator as the case requires.

The polymerization is conducted, if necessary, using a radical polymerization initiator, by gradually heating within a temperature range of from room temperature to about 130° C. or by irradiating electromagnetic waves such as microwaves, ultraviolet rays or radiation rays ($\gamma$-rays). In the case of the heat polymerization, the temperature may stepwisely be raised. The polymerization may be conducted by a bulk polymerization method or a solvent polymerization method by means of a solvent, or it may be conducted by any other method.

Specific examples of the radical polymerization initiator include, for example, azobisisobutyronitrile, azobisdimethylvaleronitrile, benzoylperoxide, tertbutylhydroperoxide and cumenehydroperoxide. These initiators may be used alone or in combination as a mixture of two or more different types. In a case where photopolymerization is employed, a photopolymerization initiator or sensitizer may preferably be added.

The amount of the polymerization initiator is preferably within a range of from 0.01 to 1 part by weight per 100 parts by weight of the total monomer mixture subjected to the polymerization.

When the ocular lens material thus obtained is shaped into ocular lenses such as contact lenses or intraocular lenses, shaping methods commonly used by those skilled in the art such as a lathe cutting and polishing method and a molding method, may be employed. For example, the lathe cutting and polishing method is a method in which the polymerization is conducted in a suitable mold or vessel to obtain a rod-, block- or plate-shaped base material (copolymer), and then the base material is processed into a desired shape by mechanical processing such as lathe cutting and polishing. The molding method is a method in which a mold corresponding to the shape of a desired ocular lens is prepared, and the polymerization of the monomer mixture is conducted in this mold to obtain a molded product, which may further be subjected to mechanical finishing treatment, if necessary. Further, when the ocular lens material of the present invention is used as an intraocular lens, a supporting portion of the lens may be prepared separately from the lens and then attached to the lens, or it may be molded simultaneously (integrally) with the lens.

Plasma treatment may be applied to the ocular lens material of the present invention, if necessary. The apparatus and method for the treatment may be those commonly employed in this technical field. As the treating conditions, it is common to employ such conditions that the treatment is conducted for from a few seconds to a few tends minutes in an inert gas atmosphere such as helium, neon or argon or in a gas atmosphere such as air, oxygen, nitrogen, carbon monoxide or carbon dioxide under a pressure of from about 0.0001 to a few Torr at a power of from a few W to about 100 W. More preferably, conditions such that the treatment is conducted in an atmosphere of air, oxygen or argon under a pressure of about from 0.05 to 3 Torr at a power of from about 10 to 60 W for a period of a few minutes, are employed.

Now, the present invention will be described in further detail with reference to Examples. However, it should be understood that the present invention is by no means restricted to such specific Examples.

EXAMPLE 1

Preparation of 4-vinylbenzyl methacrylate

Into a 1 l three necked round bottom flask equipped with a thermometer and a Dimroth condenser having a calcium chloride tube attached thereto, 300 ml of benzene and 103 g (about 1.2 mols) of methacrylic acid were charged. While cooling the mixture in an ice bath to a temperature of not higher than 10° C., 167 g (about 1.1 mols) of 1,8-diazabicyclo[5.4.0]-7-undecene was gradually dropwise added over a period of about 30 minutes by means of a dropping funnel. Then, 153 g (about 1.0 mol) of pchloromethylstyrene was gradually dropwise added over a period of about 5 minutes by means of a dropping funnel, while maintaining the temperature at a level of not higher than 10° C. Then, the ice bath was removed, and the mixture was reacted at room temperature for 24 hours.

The reaction mixture thus obtained was subjected to aspiration filtration to remove solid by-products. The filtrate was washed twice with a 5% sodium carbonate aqueous solution and then washed three times with water. The organic layer was dried overnight with anhydrous sodium sulfate. The drying agent was removed by filtration, and the organic layer was concentrated and distilled for purification. The yield of the purified product was 60%. The purified product was a colorless liquid having an aroma. The boiling point during the distillation was 105° C. (under 0.12 mmHg).

The infrared absorption spectrum and the $^1$H-nuclear magnetic resonance spectrum of the purified product were measured and analyzed, whereby this purified product was ascertained to be 4-vinylbenzyl methacrylate.

EXAMPLE 2

Preparation of a copolymer 60 parts by weight of tris(trimethylsiloxy)silylpropyl methacrylate, 40 parts by weight of trimethylsilylstyrene, 6 parts by weight of 4-vinylbenzyl methacrylate prepared in Example 1, 6.2 parts by weight of N-vinylpyrrolidone and 4.8 parts by weight of methacrylic acid were uniformly mixed, and 0.3 part by weight of azobisdimethylvaleronitrile was added to obtain a blend solution. About 50 ml of the blend solution was introduced into a glass test tube, and the test tube was closed.

Preliminary polymerization was conducted in a water bath of 35° C. for 40 hours, and then the test tube was transferred to an air circulating oven. Then, the mixture was reacted at 50° C. for 6 hours, and then the temperature was raised to 130° C. at a rate of 10° C. per from 1 to 1.5 hours, whereby the components were heat-polymerized to obtain a rod-shaped copolymer.

Then, this rod-shaped copolymer was mechanically processed by lathe cutting and polishing to obtain a test specimen. The physical properties (the appearance, the distortion, the Rockwell hardness, the oxygen permeability coefficient, the refractive index, the impact strength) of the test specimen thus obtained were measured as follows. The results are shown in Table 1.

The test specimen obtained had a transparent appearance without distortion and was suitable to obtain an ocular lens material.

Appearance

The appearance of the rod-shaped copolymer was visually observed.

Presence or absence of distortion

The presence or absence of distortion of the rod-shaped copolymer was ascertained by an optical elastic distortion meter (precision distortion meter SVP-30, manufactured by Toshiba Corporation). When no distortion was detected, the distortion was identified as "Nil", and when a white or rainbow distortion was observed, the distortion was identified as "Yes".

Rockwell hardness

The Rockwell hardness was measured using a test specimen having a diameter of 12.7 mm and a thickness of 4 mm by a Rockwell superficial hardness meter (ASD, manufactured by Kabushiki Kaisha Akashi Seisakusho) under a load of 30 kg, an indenter of 1/4 inch at 25° C.

Oxygen permeability coefficient

With respect to several test specimens having a diameter of 12.7 mm and different thicknesses, the oxygen permeability coefficients were measured in a saline at 5° C. by means of a Seikaken type film oxygen permeation measuring instrument manufactured by Rika Seiki Kogyo Kabushiki Kaisha. The unit of the numerical values in Table 1 is $$\frac{ml\ (STP) \cdot cm^2}{cm^3 \cdot sec \cdot mmHg}.$$

The numerical values in the Table are values obtained by multiplying the values of the original oxygen permeability coefficients by $10^{11}$.

Refractive index

The refractive index ($n_D{}^{20}$) of a test specimen having a diameter of 12.7 mm and a thickness of 4 mm was measured by an Abbe refractometer (1T manufactured by Atago K.K.).

Impact strength

A steel ball having a weight of 6.75 g was dropped onto a test piece having a thickness of 0.5 mm, and the height (mm) when the test piece broke was measured as the impact strength.

EXAMPLES 3 TO 9

In the same manner as in Example 2, the components as identified in Table 1 were uniformly mixed and polymerized to obtain a copolymer, and a test specimen was prepared therefrom, and various physical properties were measured in the same manner. The results are shown in Table 1.

COMPARATIVE EXAMPLES 1 TO 5

In the same manner as in Example 2, a test specimen was prepared by a blend composition as shown in Table 1 using a conventional cross linking agent (ethylene glycol dimethacrylate, divinylbenzene, allyl methacrylate, or trimethylolpropane trimethacrylate), and various physical properties were measured in the same manner. The results are shown in Table 1.

Symbols used in Table 1

SiMA: Tris(trimethylsiloxy)silylpropyl methacrylate
SiSt1: Trimethylsilylstyrene
SiSt2: Tris(trimethylsiloxy)silylstyrene
6FP 2,2,2,2', 2', 2'-hexafluoroisopropyl methacrylate
VBMA: 4-vinylbenzyl methacrylate
EDMA: Ethylene glycol dimethacrylate
DVBz: Divinylbenzene
AMA: Allyl methacrylate
TMP: Trimethylolpropane trimethacrylate
N-VP: N-vinylpyrrolidone
MAA: Methacrylic acid
MMA: Methyl methacrylate
V-65: Azobisdimethylvaleronitrile

TABLE 1

| | Example No. |
|---|---|

TABLE 1-continued

| | Example No. | | | | | | | | Comparative Example 1 | Comparative Example 2 |
|---|---|---|---|---|---|---|---|---|---|---|
| | 2 | 3 | 4 | 5 | 6 | 7 | 8 | 9 | | |
| Blend component (parts by weight) | | | | | | | | | | |
| (Meth)acrylic monomer | SiMA 60 MAA 4.8 | 6FP 54 MAA 4.8 | 6FP 35 MAA 4.8 | 6FP 35 MAA 4.8 | 6FP 35 MAA 4.8 | 6FP 17 MAA 4.8 | 6FP 6 MMA 30 SiMA 4 MAA 4 | 6FP 7 MMA 15 SiMA 5 MAA 4 | SiMA 60 MAA 4.8 | 6FP 54 MAA 4.8 |
| Styrene monomer | SiSt1 40 | SiSt2 46 | SiSt2 65 | SiSt2 65 | SiSt2 65 | SiSt2 83 | SiSt2 46 | SiSt2 61 | SiSt1 40 | SiSt2 46 |
| Other monomer | N-VP 6.2 | N-VP 6.2 | N-VP 6.2 | N-VP 6.2 | N-VP 6.2 | N-VP 6.2 | | | N-VP 6.2 | N-VP 6.2 |
| Cross linking agent | VBMA 6 | VBMA 6 | VBMA 3 | VBMA 6 | VBMA 9 | VBMA 6 | VBMA 10 | VBMA 8 | EDMA 6 | EDMA 6 |
| Polymerization initiator | V-65 0.3 | V-65 0.3 | V-65 0.3 | V-65 0.3 | V-65 0.3 | V-65 0.3 | V-65 0.3 | V-65 0.3 | V-65 0.22 | V-65 0.3 |
| Physical properties | | | | | | | | | | |
| Appearance | Transparent | Transparent | Transparent | Transparent | Transparent | Transparent | Transparent | Transparent | Turbid | Turbid |
| Distortion | Nil | Nil | Nil | Nil | Nil | Nil | Nil | Nil | Yes | Yes |
| Rockwell hardness (30X) | 40 | 58 | 38 | 45 | 49 | 39 | 76 | 61 | 35 | 56 |
| Oxygen permeability coefficient | 125 | 209 | 260 | 247 | 230 | 270 | 60 | 101 | 121 | 170 |
| Refractive index | 1.488 | 1.436 | 1.447 | 1.449 | 1.454 | 1.450 | 1.468 | 1.462 | 1.483 | 1.434 |
| Impact strength | 35 | 34 | 29 | 37 | 38 | 31 | 31 | 27 | 34 | 30 |

| | Example No. | | |
|---|---|---|---|
| | Comparative Example 3 | Comparative Example 4 | Comparative Example 5 |
| Blend component (parts by weight) | | | |
| (Meth)acrylic monomer | 6FP 54 MAA 4.8 | 6FP 54 MAA 4.8 | 6FP 54 MAA 4.8 |
| Styrene monomer | SiSt2 46 | SiSt2 46 | SiSt2 46 |
| Other monomer | N-VP 6.2 | N-VP 6.2 | N-VP 6.2 |
| Cross linking agent | DVBz 6 | AMA 6 | TMP 6 |
| Polymerization initiator | V-65 0.3 | V-65 0.3 | V-65 0.3 |
| Physical properties | | | |
| Appearance | Turbid | Slightly turbid | Turbid |
| Distortion | Yes | Slightly yes | Yes |
| Rockwell hardness (30X) | 51 | 20 | 59 |
| Oxygen permeability coefficient | 180 | 187 | 175 |
| Refractive index | 1.437 | 1.434 | 1.435 |
| Impact strength | 21 | 15 | 28 |

As is evident from the comparison of Examples and Comparative Examples, with respect to the ocular lens material obtainable by copolymerizing a (meth)acrylic monomer and a styrene monomer, in the Examples of the present invention, the appearance was transparent without distortion, and the material had no problem as an ocular lens material. Whereas, in Comparative Examples 1 to 3 and 5 wherein conventional cross linking agents were used, the appearance was turbid and a distortion was observed, and the products were not suitable as optical lens materials. In Comparative Example 4, the product was substantially transparent, and the distortion was less than those in other Comparative Examples, but inferior to those in the Examples of the present invention, and the hardness and the impact strength were also lower than those in the Examples of the present invention, and thus an ocular lens material having satisfactory physical properties was not obtained.

Further, among them, an ocular lens material containing a silicon-containing styrene derivative and a fluorine-containing (meth)acrylate and the vinylbenzyl (meth)acrylate as the main components (particularly Examples 3 to 7), is a material which is optically transparent without distortion and has a high refractive index and excellent mechanical strength and hardness and thus has excellent durability against an impact and which has an extremely high oxygen permeability with an oxygen permeability coefficient of at least 200 (the unit is the same as in Table 1). Thus, this optical lens material is suitable for use as a contact lens material.

It is evident from the comparison in the oxygen permeability coefficients between Example 3 and Comparative Examples 2 to 5 that the oxygen permeability coefficients in the Comparative Examples are all lower than 190 (the unit is the same as in Table 1) and inferior to the oxygen permeation coefficient in Example 3, in spite of the fact that in each Example, the copolymer was composed of the same composition except that the cross linking agent used was different.

The ocular lens material of the present invention is a strong copolymer with a cross linked network structure formed by the linking agent of the formula I and is optically transparent without distortion. Particularly an ocular lens material of the present invention comprising a styrene monomer and a (meth)acrylate monomer as the copolymer components, is an ocular lens material which is tough and excellent in the mechanical strength and hardness, is transparent without distortion and has excellent optical properties.

Among them, a material containing a silicon-containing styrene derivative and a fluorine-containing (meth)acrylate and the vinylbenzyl (meth)acrylate as the main components, is a material which is optically transparent without a distortion and has a high refractive index and excellent mechanical strength and hardness and thus is excellent in the durability against an impact and which has an extremely high oxygen permeability. Thus, it is suitable for use as a contact lens material.

What is claimed is:

1. An ocular lens material, which is a copolymer comprising a cross linking agent of formula I

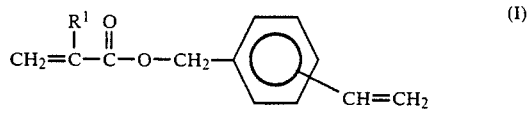

wherein $R^1$ is a hydrogen atom or a methyl group, a styrene monomer, and an acrylic monomer and/or a methacrylic monomer.

2. The ocular lens material according to claim 1, which is a contact lens material comprising the cross linking agent of the formula I, a silicon-containing styrene derivative, and a fluorine-containing acrylate and/or a fluorine-containing methacrylate.

3. The ocular lens material according to claim 1, wherein the content of the cross linking agent of the formula I is from 0.5 to 15 parts by weight in 100 parts by weight of the total copolymer components.

4. The ocular lens material according to claim 1, wherein the content of the cross linking agent of the , formula I is from 0.5 to 15 parts by weight in 100 parts by weight of the total copolymer components.

5. The ocular lens material according to claim 2, wherein the content of the cross linking agent of the formula I is from 0.5 to 15 parts by weight in 100 parts by weight of the total copolymer components.

* * * * *